US 6,337,213 B1

(12) United States Patent
Simon et al.

(10) Patent No.: US 6,337,213 B1
(45) Date of Patent: Jan. 8, 2002

(54) APPARATUS AND METHOD FOR COLLECTION AND CONCENTRATION OF RESPIRABLE PARTICLES INTO A SMALL FLUID VOLUME

(75) Inventors: Jonathan N. Simon, San Leandro; Steve B. Brown, Livermore, both of CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/456,341

(22) Filed: Dec. 8, 1999

Related U.S. Application Data

(60) Provisional application No. 60/113,067, filed on Dec. 21, 1998.

(51) Int. Cl.[7] .................................................. G01N 1/18
(52) U.S. Cl. ..................... 436/178; 436/177; 436/181; 422/68.1; 422/83; 422/88; 422/101; 55/423
(58) Field of Search .......................... 422/68.1, 72, 83, 422/88, 101; 436/45, 174, 177, 178, 181; 55/423, 428

(56) References Cited

U.S. PATENT DOCUMENTS

| | | | | |
|---|---|---|---|---|
| 3,857,687 A | * | 12/1974 | Hamilton et al. | ............. 55/337 |
| 4,350,507 A | * | 9/1982 | Greenough et al. | ...... 73/863.23 |
| 4,654,054 A | * | 3/1987 | Snaddon et al. | ................ 96/68 |
| 4,942,135 A | * | 7/1990 | Zaromb | ...................... 436/178 |
| 4,961,916 A | * | 10/1990 | Lesage et al. | ................ 422/88 |
| 4,977,095 A | * | 12/1990 | Zaromb | ...................... 436/178 |
| 5,173,264 A | * | 12/1992 | Zaromb et al. | ............... 422/88 |
| 5,328,851 A | * | 7/1994 | Zaromb | ...................... 436/178 |
| 6,087,183 A | * | 7/2000 | Zaromb | ...................... 436/178 |

FOREIGN PATENT DOCUMENTS

DE  29813282  * 12/1999

OTHER PUBLICATIONS

Woo et al. *Environmental Science & Technology*, vol. 32, No. 1 pp. 169–176, 1998.*

A. Birenzvige et al, A Portable High–Throughput Liquid––Absorption Air Sampler for Respirable Aerosol Particles, Aerosol Science and Technology, 29: 133–140 (1998).

* cited by examiner

*Primary Examiner*—Maureen M. Wallenhorst
(74) *Attorney, Agent, or Firm*—L. E. Carnahan; Alan H. Thompson

(57) ABSTRACT

An apparatus and method for the collection of respirable particles and concentration of such particles into a small fluid volume. The apparatus captures and concentrates small (1–10 $\mu$m) respirable particles into a sub-millileter volume of fluid. The method involves a two step operation, collection and concentration: wherein collection of particles is by a wetted surface having small vertical slits that act as capillary channels; and concentration is carried out by transfer of the collected particles to a small volume (sub-milliliter) container by centrifugal force whereby the particles are forced through the vertical slits and contact a non-wetted wall surface, and are deflected to the bottom where they are contained for analysis, such as a portable flow cytometer or a portable PCR DNA analysis system.

20 Claims, 3 Drawing Sheets

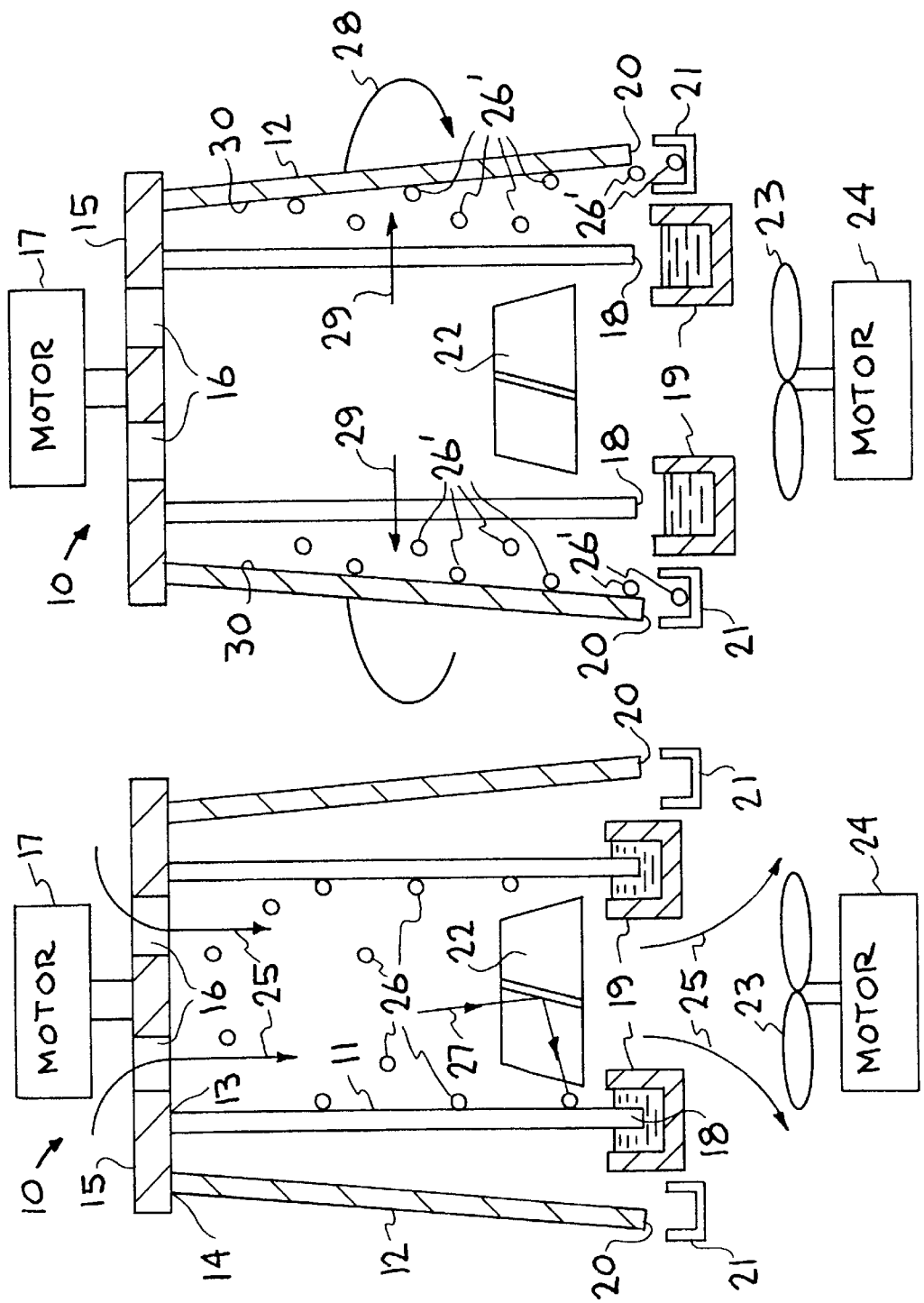

APPARATUS AND METHOD FOR COLLECTION AND CONCENTRATION OF RESPIRABLE PARTICLES INTO A SMALL FLUID VOLUME

RELATED APPLICATION

This application relates to U.S. Provisional Application No. 60/113,067 filed Dec. 21, 1998, and claims priority thereof.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to sample collection of particles, particularly to the collection and concentration of small (1–10 μm) respirable particles for analysis, and more particularly to a low power, man-portable apparatus to capture and concentrate small respirable particles into a sub-milliliter volume of fluid for analysis.

Substantial development work has been done in recent years on portable Polymerase Chain Reaction (PCR) and cytometric detectors with the ultimate goal of producing man-portable biological agent detection systems. At the front end of these systems is a sample collector, which collects and concentrates the agents of interest into a liquid sample volume. The agents sampled are generally in the form of respirable particles with sizes in the range of 1–10 μm.

The sample collectors now used with mini PCRs and mini-flow cytometers are large (typically several liters in volume), requiring relatively large fans which draw too much power for portable use. These prior collectors concentrate their sample into milliliter (mL) size volumes, and are inefficient for low-concentration samples. Detectors and their associated sample volumes are becoming smaller (<100 μL for PCR), so currently available mL sample volumes are much too large. A recent approach to a small sample collector is described in "A Portable High-Throughout Liquid-Absorption Air Sampler for Respirable Aerosol Particles", A. Birenzvige et al, Aerosol Science and Technology, 29: 133–140 (1998). In this approach, a liquid extractant was injected into a conical cavity and a fan was then activated so as to draw air into the cavity, whereby the highly turbulent and swirling motion of the air caused the liquid to swirl up and wet the wall of the sampling tube such that particles in the air collected in the liquid, and after a few minutes the fan was shut off and the liquid drained for analysis. While the above described sample collector reduced the sample volume size, the collection apparatus is complex, expensive, and has low efficiency.

An ideal sample collector, for aerosol liquids, airborne pathogens, or other small particles of interest, should be low power, man-portable, inexpensive, and can concentrate the sample into a volume less than 100 μL. The present invention provides a solution to the above reference need for a small volume sample collector, and involves an apparatus and method to capture and concentrate small (1–10 μm) respirable particles into a sub-milliliter volume of fluid, and thus provides a sample collector wherein the fluid volume with concentrated particles is small and compatible with current mini-PCRs and mini-flow cytometers. The method of the invention is of a two step, or phase operation, inspiration and concentration, where the inspiration step basically collects particles on a wetted wall having small slits therein that act as capillary channels, and the concentration step basically involves spinning the wetted wall to drive the particles and fluid through the small slits and such impinge on a non-wetted surface and slide off into a container. The basic difference in this apparatus and methods from previous approaches is that the collection phase uses a fixed volume defined by the capillary slits, and the amount of particles collected in the concentration phase is determined by the sampling time.

SUMMARY OF THE INVENTION

It is an object of the present invention to provide a small volume sample collector.

A further object of the invention is to provide a small volume, low power, man-portable sample collector for small particles of interest.

A further object of the invention is to provide for the capture and concentration of 1–10 μm size respirable particles into a sub-milliliter volume of fluid.

Another object of the invention is to provide a two phase method of collecting and concentrating small particles into a small volume fluid sample.

Another object of the invention is to provide a sample collector having wetted capillary channels, and a concentrator that forces the collected particle by centrifugal force through the capillary channels into a container.

Another object of the invention is to provide a man-portable, small fluid volume, sample collector and concentrator for 1–10 μm size particles of interest that is compatible with mini-PCRs or mini-flow cytometers.

Another object of the invention is to provide a man-portable, small fluid volume particle collector and concentrator wherein the collection phase uses a fixed volume, defined by capillary slits, and the concentration phase is determined by the sampling time.

Other objects and advantages of the present invention will become apparent from the following description and accompanying drawings. Basically the invention involves a low power, man-portable, small fluid volume sample collector for 1–10 μm size aerosol liquids, airborne pathogens, or other small particles of interest. The invention involves an apparatus and method to capture and concentrate small (1–10 μm) respirable particles into a sub-milliliter volume of fluid. The method is a two step or phase operation involving first collection and second concentration. The collection (inspiration) phase involves a cylindrical liner with small vertical slits that act as capillary channels connected to a fluid reservoir and provide a wetted surface to trap particles present in air being blown through the cylindrical liner. The concentration phase involves a transfer operation wherein the cylindrical liner is spun and the collected sample volume is forced through the capillary channels and against a non-wetted surface that deflects the sample to the bottom of the device where it is collected. The collection phase uses a fixed volume, defined by the capillary slits, and the concentration is determined by the sampling time. Thus, to get a higher concentration of particles into the sample, the inspiration step is longer, but the sample size stays the same.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1 schematically illustrates an embodiment of an apparatus made in accordance with the present invention operating in the collection (inspiration) phase of the method of the invention.

FIG. 2 illustrates the apparatus of FIG. 1 in the concentration phase of the method of the invention.

DETAILED DESCRIPTION OF THE INVENTION

Figure 3:
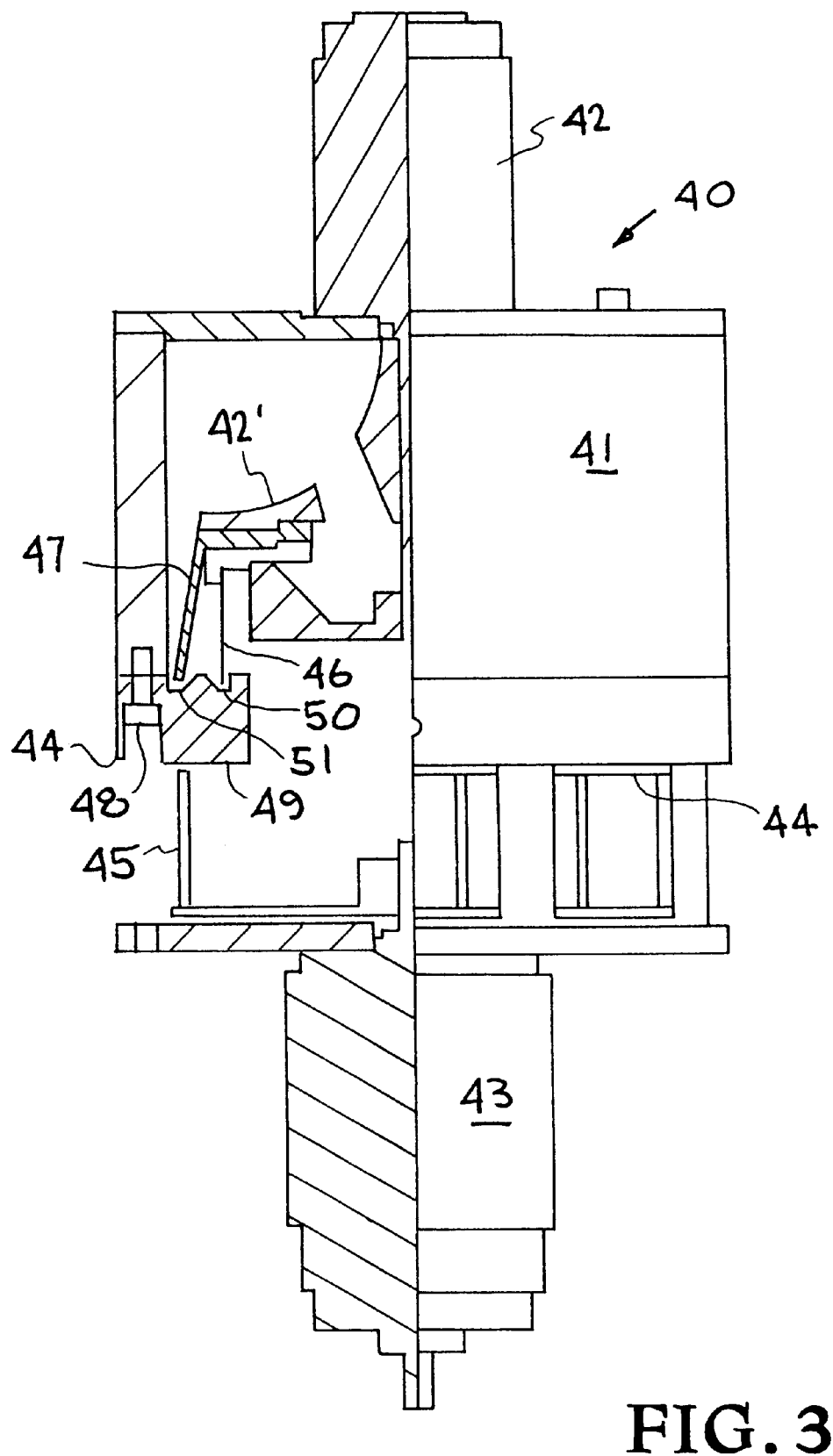
FIG. 3 illustrates another embodiment of the apparatus of the present invention.

The present invention is directed to an apparatus and method for the collection of respirable particles and concentration of said particles into a small fluid volume. The apparatus is of a man-portable type and designed to capture and concentrate small (1–10 $\mu$m) aerosol liquids, airborne pathogens, or other particles of interest into a sub-milliliter volume of fluid. The fluid with concentrated particles can then be analyzed by a portable flow cytometer or PCR DNA analysis system. Thus, the invention provides a solution for the need of a low power, man-portable sample collector which can concentrate the sample into a volume less than 100 $\mu$L.

The method of the invention involves a two step or phase process. In the first phase or step, referred to herein as "inspiration" or collection, a fan draws turbulent air into a central cylinder that is lined along its circumference with small vertical slits that act as capillary channels. The capillary channels are connected to a central fluid reservoir and provide a wetted surface to trap particles in the air. The reservoir will also replenish fluid as it evaporates. Fouling of the system by larger particles may be minimized by a pre-collection fractionator. The inspiration step or phase lasts for several minutes, the length of this phase determines the concentration of the particles into the sample.

In the second step or phase referred to herein as "transfer" or concentration, at least the central cylinder is spun, and the sample volume is forced out of the capillary channels by centrifugal force. Alternately, the cylinder may be pressurized, or a containing vessel evacuated to force the liquid out of the slits. The liquid impinges on a non-wetting cylindrical surface, located about the central cylinder, that deflects the liquid to the bottom of the device where it is finally collected.

Sample collectors, as currently known use a continuous stream of fluid to capture particles. This means that for a low concentration sample, a large volume must be collected to get enough of the target particles to be sensed. For the sample to be used in very small volume sensors (such as a mini-PCR), this means subdividing the collected sample into smaller portions, greatly reducing the effect of concentration. The basic difference in the current collector/concentrator with the prior known approaches, is that in this current device the collection or inspiration phase uses a fixed volume, defined by the capillary slits, and the concentration factor of the particles is determined by the sampling time. This means that to get a higher concentration of particles into the sample, the inspiration (collection) phase or step is longer, but the sample size stays the same.

The apparatus of the invention basically comprises a pair of cylinders with the central cylinder having small vertical slits in the wall, the lower end being in contact with a liquid reservoir, and being mounted within an outer cylinder having an unwetted tapering surface. A fan directs air into the central cylinder. The central cylinder is spun causing the liquid sample to be driven from the slits therein onto the inner surface of the outer cylinder which deflects the sample into a collection container. The outer cylinder may be held stationary or spun with the central cylinder. Depending on the construction and cooperation of the central cylinder and the reservoir, it may be necessary to lower the reservoir prior to spinning of the central cylinder.

Referring now to the drawings, FIGS. 1 and 2 schematically illustrate the overall operation or method of the invention which involves an inspiration (collection) cycle and a spin (concentration) cycle, respectively. In the inspiration cycle, fractionated air is drawn through a central cylinder having capillary slits and which are connected to a fluid reservoir, particles stick to fluid in the capillary slits (100 $\mu$m×100 $\mu$m×50 mm slit=0.5 $\mu$l fluid), and evaporating fluid in the slits is replenished from the reservoir. In the spin cycle, the air passing through the central cylinder is shut off and the cylinder, if necessary, is separated from the fluid reservoir, the central cylinder is then spun forcing fluid and captured particles through the capillary slits, and the captured particles and fluid move outward and contact an outer capture frustum, cylinder or cone and pass down the inner surface thereof to a collection point at the bottom of the cone, whereafter the collected particles can be analyzed, such as by a portable flow cytometer or PCR. The capillary size affects the spin speed requirement and sample volume, and a small intake fan can be utilized to draw the air through the central cylinder.

Figure 4:
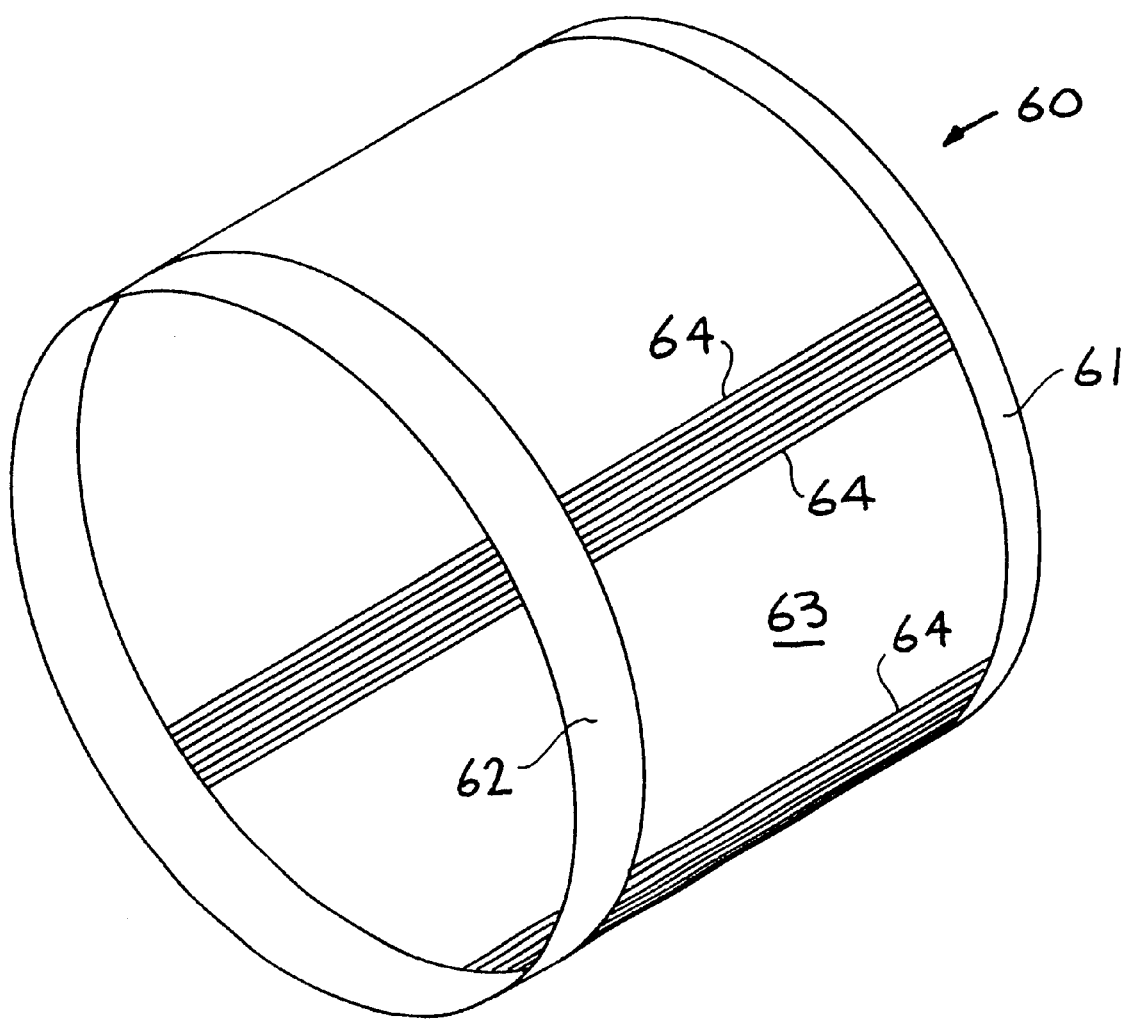
FIG. 4 illustrates an embodiment of the central cylinder of the apparatus of FIG. 1 showing a portion of the vertical capillary slits which are located around the circumference of the cylinder.

As shown in the schematic embodiment of FIGS. 1 and 2, the collection/concentration apparatus generally indicated at 10 comprises a central cylinder 11, and an outer cylinder 12 having an upper end of each indicated at 13 and 14, mounted to a member 15 having openings 16 (tub shown) and to which a spin motor 17 is mounted. A lower end 18 of central cylinder 11, as shown in FIG. 1, extends into a fluid or liquid reservoir 19, while a lower end 20 of outer cylinder 12 is located above a collector or container 21. An optional deflector 22 is positioned within central cylinder 11 and a suction impeller or fan 23 driven a motor 24 is located beneath the central cylinder 11. Central cylinder 11 is provided with vertically extending slits about the circumference thereof which function as capillary channels. FIG. 4 illustrates in greater detail an embodiment of the central cylinder 11.

The method of the present invention involves a two phase or step operation. In the first phase or step, the collection or inspiration operation, the fan 23 draws turbulent air through the central cylinder 11, as indicated by arrows 25, cylinder 11 being lined along its circumference with small vertical slits that act as capillary channels. The capillary channel in central cylinder 11 is connected to the reservoir 19 and provide a wetted surface to trap particles 26 present in the air. The reservoir 19 will also replenish fluid as it evaporates. Note that deflector 22 functions to direct particles 26 as indicated by arrow 27 onto the inner (or capillary) surface 27 of central cylinder 11 where they are trapped in liquid in the capillary slits.

After the inspiration step, shown in FIG. 1, which may last for several minutes, there is a transfer or collection step, shown in FIG. 2. As shown, the air flow, through central cylinder 10 is shut off and the reservoir 19 is lowered from the end 18 of central cylinder 11, after which the cylinders 11 and 12 are spun by motor 17 as indicated by arrow 28. In some cases, only central cylinder 11 needs to be spun. As the central cylinder 11 is spun, the sample volume (particles 26 trapped in liquid) is forced outwardly through the capillary channels in cylinder 11, as indicated by arrows 29, by centrifugal force. The particle containing liquid droplets 26' impinges on a non-wetting inner wall surface 30 of outer cylinder 12 that deflects the droplets 26' to the bottom and 20 of cylinder 12 where they are collected by collector on container 21 for analysis as described above.

Alternately, the central cylinder 11 may be pressurized or the outer cylinder 12 may be evacuated to force the particle container liquid droplets 26' through the capillary slits in the wall of central cylinder 11.

As pointed out above, the apparatus of FIGS. 1 and 2 provides a collection phase using a fixed volume, defined by the capillary slits, and concentration of the particles is determined by the sampling time. Thus, to get a higher concentration of particles into the sample, the inspiration step is longer, but the sample size stays the same.

FIG. 3 illustrates an embodiment of the apparatus which incorporates the components of the schematic embodiment of FIGS. 1 and 2. The apparatus, generally indicated at 40 includes a housing 41 on which is mounted a spin motor 42 and a fan or impeller motor 43. Housing 41 is provided with slots or openings 44 adjacent motor 43 and within the housing 41 is mounted an impeller 45 connected to be driven by motor 43. Spin motor 42 is operatively connected by a mechanism generally indicated at 42' to a capillary slit containing cylinder 46 and a non-wettable cylinder or capture cone 47 located within housing 41. Mounted to housing 41, as by bolts 48, only one shown, is an annular member 49 containing annular grooves 50 and 51, with groove 50 functioning as a fluid reservoir to supply fluid to the slits in cylinder 46, and groove 51 functioning as a collector or container for particle containing fluid droplets. The components of the apparatus of FIG. 3 function as described above with respect to FIGS. 1 and 2.

FIG. 4 illustrates an embodiment of the central cylinder 11 of FIGS. 1–2 and 46 of FIG. 3, and is generally indicated at 60. Cylinder 60 includes annular outer rim sections 61 and 62 connected by an annular wall section 63 having vertically extending slits 64 around the circumference of wall section 63, only partially illustrated. Rim section 62 may be provided with an outwardly flange or lip, not shown, extending illustration. By way of example, the cylinder 50 may have an overall length of 1.250 inch, an outer diameter or width of 1.00 inch, with rim section 61 having a length of 0.150 inch, and rim section 62 having a length of 0.100 inch, with the slits 64 having a width of 10 $\mu$m to enable passage of particle containing fluid droplets of 1–10 $\mu$m. An embodiment of a tested cylinder had a height of ½", diameter of 2", with slits of 75 $\mu$m. The slits may be 50–75 $\mu$m for example.

It has thus been shown that the present invention provides an apparatus and method for collecting and concentrating particles in the range of 1–10 microns, and can concentrate the sample into a volume less than 100 $\mu$L. Thus, this invention enables collection and concentration of small (1–10 $\mu$m) particles that can be analyzed by a portable flow cytometer or PCR DNA analysis system. The apparatus of the invention provides a low power, manportable collector/concentrator, thus providing a solution to the need for such an apparatus.

While particular embodiments and parameters have been illustrated and/or described to exemplify and teach the principles of the invention, such are not intended to be limiting. Modifications and changes may become apparent to those skilled in the art, and it is intended that the invention be limited only by the scope of the appended claims.

What is claimed is:

1. Apparatus for collection and concentration of particles, comprising:

a central cylindrical member having vertically extending slots therein, a cylindrical member positioned around said central cylindrical member having a non-wetted inner surface, a fluid reservoir, said central cylindrical member having one end contacting an associated fluid contained in said reservoir so that the vertically extending slots are wetted, a collector positioned adjacent one end of said cylindrical member, means for passing air through said central cylindrical member and causing particles in the air to become trapped in the wetted slots, and means for rotating at least said central cylindrical member, wherein said means for rotating forces the trapped particles out of the wetted slots so as to impinge on the non-wetted inner surface of the cylindrical member and deflect towards the collector.

2. The apparatus of claim 1, additionally including means located in said central cylindrical member for deflecting air passing therethrough onto said vertically extending slots of said central cylindrical member.

3. The apparatus of claim 1, wherein said means for rotating is operatively connected to both of said cylindrical members.

4. The apparatus of claim 1, wherein said means for passing air through said central cylindrical member comprises a motor drive impeller.

5. The apparatus of claim 1, wherein said means for rotating at least said central cylindrical member includes a motor.

6. The apparatus of claim 1, additionally including a housing enclosing at least both said cylindrical members, said fluid reservoir, and said collector.

7. The apparatus of claim 6, wherein said means for passing air through said central cylindrical member and said means for rotating at least said central cylindrical member are positioned on opposite sections of said housing.

8. The apparatus of claim 7, wherein said housing includes a plurality of openings, and wherein said means for passing air through said central cylindrical member includes an impeller located within said housing and adjacent said openings.

9. The apparatus of claim 6, additionally including a member located within said housing and having a pair of spaced grooves therein defining said fluid reservoir and said collector.

10. The apparatus of claim 1, wherein said central cylindrical member has an annular wall section having said vertically extending slots located around the circumference thereof, and a pair of annular end sections located on opposite ends of said annular wall section.

11. The apparatus of claim 10, wherein said vertically extending slots have a width of greater than about 10 $\mu$m.

12. The apparatus of claim 1, wherein said vertically extending slots in said central cylindrical member have a width of 10–75 $\mu$m.

13. A method for capturing and concentrating 1–10 $\mu$m respirable particles into a sub-milliliter of fluid, comprising:

a collection phase which includes trapping the particles in wetted capillary channels, and a transfer phase which includes forcing the trapped particles out of the wetted capillary channels onto a non-wetted wall surface, and collecting the particles deflected from the non-wetted wall surface.

14. The method of claim 13, wherein forcing the trapped particles out of the wetted capillary channels is carried out by a procedure selected from the group consisting of centrifugal force, pressurization, and evacuation.

15. The method of claim 13, wherein the trapping of the particles is carried out by directing air containing the particles through a member having the wetted capillary channels formed therein.

16. The method of claim 15, additionally including forming the member in a cylindrical configuration and providing vertically extending slots in said cylindrical member to form the wetted capillary channels.

17. The method of claim 16, additionally including providing a fluid reservoir positioned such that an end of the cylindrical member contacts an associated fluid in the reservoir for maintaining fluid in the vertically extending slots.

18. The method of claim 17, additionally including providing means for deflecting the air containing particles onto the vertically extending slots, wherein the means for deflecting is located in the cylindrical member.

19. The method of claim 18, additionally including providing another member surrounding and in spaced relation to the cylindrical member, wherein said another member contains the non-wetted wall surface for deflecting the trapped particles forced out of the wetted capillary channels to enable collection thereof.

20. The method of claim 19, additionally including providing a means located adjacent an end of the another member for collecting the deflected particles.

* * * * *